(12) United States Patent
Ballsieper

(10) Patent No.: US 7,294,845 B2
(45) Date of Patent: Nov. 13, 2007

(54) RADIATION PROTECTION ARRANGEMENT COMPRISING A SEPARABLE COVER

(75) Inventor: Barbara Ballsieper, Taufkirchen (DE)

(73) Assignee: Mavig GmbH, Munich (DE)

( * ) Notice: Subject to any disclaimer, the term of this patent is extended or adjusted under 35 U.S.C. 154(b) by 0 days.

(21) Appl. No.: 10/559,397

(22) PCT Filed: Mar. 22, 2004

(86) PCT No.: PCT/EP2004/003027

§ 371 (c)(1),
(2), (4) Date: Dec. 5, 2005

(87) PCT Pub. No.: WO2004/107979

PCT Pub. Date: Dec. 16, 2004

(65) Prior Publication Data

US 2006/0124871 A1    Jun. 15, 2006

(30) Foreign Application Priority Data

Jun. 5, 2003   (DE) ................................ 103 25 567

(51) Int. Cl.
*G21F 3/02* (2006.01)
(52) U.S. Cl. .............................. 250/516.1; 250/515.1; 250/505.1; 250/519.1; 378/189; 378/167; 128/857; 2/410; 2/15

(58) Field of Classification Search ..................... None
See application file for complete search history.

(56) References Cited

U.S. PATENT DOCUMENTS

| 4,196,355 | A | | 4/1980 | Maine | |
|---|---|---|---|---|---|
| 5,012,114 | A | * | 4/1991 | Sisson, Jr. | 250/519.1 |
| 5,247,182 | A | * | 9/1993 | Servant et al. | 250/516.1 |
| 5,379,332 | A | * | 1/1995 | Jacobson | 376/287 |
| 6,448,571 | B1 | * | 9/2002 | Goldstein | 250/515.1 |

FOREIGN PATENT DOCUMENTS

| DE | 33 38 122 A | 5/1985 |
|---|---|---|
| WO | WO 02/064207 | 8/2002 |

* cited by examiner

*Primary Examiner*—Jack I. Berman
*Assistant Examiner*—Zia R. Hashmi
(74) *Attorney, Agent, or Firm*—Scully, Scott, Murphy & Presser, P.C.

(57) ABSTRACT

The invention related to a radiation protection arrangement for screening radiation emitted from a radiation source, especially an x-ray source. Said arrangement is provided with a screening element consisting of, or comprising, a radiation protection material, and a cover, which fully surrounds the screening element. Said cover can be pulled over the screening element and completely separated from the same. As the cover can be changed, the radiation protection arrangement can be kept clean and sterile in a simple manner.

23 Claims, 4 Drawing Sheets

RADIATION PROTECTION ARRANGEMENT COMPRISING A SEPARABLE COVER

The present invention relates to a radiation protection arrangement, in particular an arrangement for screening the X-rays emitted by an X-ray source, which is provided for example for use at an angiographic workstation.

To keep the radiation exposure caused by X-ray examinations as low as possible for those persons involved, it has long been known to use clothing for protection against radiation. A two-part garment for protection against radiation which is known for example from U.S. Pat. No. 4,196,355 comprises a vest for protecting the upper body and a skirt for protecting the lower body, the vest and skirt including or comprising a material which screens X-rays. The persons responsible for taking X-rays, for example the doctor or an assistant, wear the vest and skirt during the examinations so that they are protected from the X-rays.

Although the known clothing for protection against radiation offers a very effective protection against excessive exposure to radiation in some cases, at angiographic workstations, as they are called, the protection which can be achieved with them is not adequate. The radiation exposure to personnel carrying out the procedure is particularly high at a workstation of this kind as a result of the multidirectional nature of the radiation, so merely wearing clothing for protection against X-rays cannot ensure the best possible radiation protection. Accordingly, appropriate additional devices for minimizing the exposure to radiation are required.

The duty of minimization laid down by the German Radiological Protection Ordinance in this context provides that the dose limit values should not only be observed but as far as possible should not even be reached. It is therefore known to use what are called lower body protection arrangements which are arranged to the side of the table on which the patient lies. In a simple construction, a lower body protection system of this kind comprises a screening blanket in the form of a lead rubber blanket or lead sheet which is encased in PVC and has a lead equivalence value of 0.5 mm which reaches from the level of the table to the floor and protects the lower extremities of the personnel carrying out the procedure, which are not covered by the clothing for protection against X-rays, from scattered radiation. In this case, the lead equivalence value describes the absorption behavior of a body, in particular a laminate, which provides the same screening from X-rays as a lead panel of that thickness. A material having a lead equivalence value of 0.5 mm therefore corresponds to screening with lead which is 0.5 mm thick.

In a particular construction, the lower body protection arrangement described above comprises a plurality of PVC lead rubber slats which are arranged laterally next to one another and at least partly overlapping. Moreover, to optimize the radiation protection, what are called radiation protection panels are used, which are arranged in the upper region of the treatment station and protect the head and upper body of the personnel carrying out the procedure, in particular their eyes, thyroid gland and acromioclavicular joint. On the underside of radiation protection panels of this kind, additional PVC lead rubber blankets may also be arranged to further improve the screening.

When the lower body protection arrangements described above are used, it must be taken into account that these systems are frequently contaminated during use with bodily fluids, contrast media or other non-sterile liquids. However, cleaning the lead rubber blankets or lead rubber slats is complex and expensive, since it is imperative not to damage the lead sheets during the work. In particular the conventional processes for sterilization by boiling or using an autoclave or by steam-cleaning in a protective atmosphere with an appropriate gas mixture are not suitable, since the screening material could be damaged by high temperatures and hence the protective function could no longer be reliably guaranteed.

A further problem area lies in the fact that the screening blankets used for lower body protection are of a fixed length, whereas the treatment table on which they are arranged and secured is adjustable in height within a range of approximately 70 cm to approximately 120 cm. This means that the best possible protection over the entire height is only guaranteed by the lead rubber blankets at a particular position of the treatment table. However, if the table is at a higher position, the lower regions of the legs of the personnel carrying out the procedure are no longer protected. By contrast, if the table is in a lower position, the lead rubber blankets cover the entire height of the table but the lower ends of the blankets lie on the floor, and in this position they are at particular risk from soiling, since the floor in the vicinity of the treatment or operating table is often covered with liquids. Furthermore, there is a risk of damage through stepping on them.

Accordingly, the present invention has the object of providing a way of keeping radiation protection arrangements of the type described above clean and sterile in the simplest possible manner.

This object is achieved by a radiation protection arrangement in accordance with claim 1 and by a cover in accordance with claim 19.

The arrangement according to the invention substantially comprises two elements, on the one hand a screening element which comprises or contains the radiation protection material, and on the other a cover which completely surrounds the screening element and may be pulled over the screening element and completely separated from the screening element.

Using a cover which is matched in its shape to the screening element and yet completely separate therefrom ensures that the screening element, which can itself only be cleaned and sterilized in a complex and expensive procedure, can be used in a sterile environment—such as an operating theatre—without itself having to be cleaned intensively after every use. Instead, it is sufficient to take away the removable cover and replace it with a clean cover, which may even be done while the procedure is under way. In this case, the cover comprises a material which, like conventional theatre gowns, can be sterilized in a suitable device quickly and in a standard procedure. For the screening element, by contrast, it is sufficient to clean only the surface thereof and to rub it down with a disinfectant. Moreover, the cover also provides a certain protection which protects the screening element from unintentional damage—for example from a scalpel.

In accordance with a particularly advantageous further development of the present invention, the cover has means with the aid of which the arrangement comprising the cover and the screening element received therein is adjustable in length, which is done by turning up or tying up the cover. As a result of this, the length of the radiation protection arrangement can be adjusted individually and can for example be matched to the respective height position of the treatment table. The problem area described above, that the arrangement is too short to guarantee adequate protection or is too long and so lies on the floor, is thus obviated.

The arrangement can be fixed in the turned-up form for example by press studs arranged on the cover, a hook-and-burr closure or a tie closure. The important point here is that the elements required to fix the arrangement are arranged exclusively on the cover and not on the screening element. This is because it is disadvantageous to attach press studs or other closures to the screening element, because this could damage the lead sheet required to screen the X-rays.

The invention will be explained below in more detail with reference to the attached drawing, in which.

Figure 1:
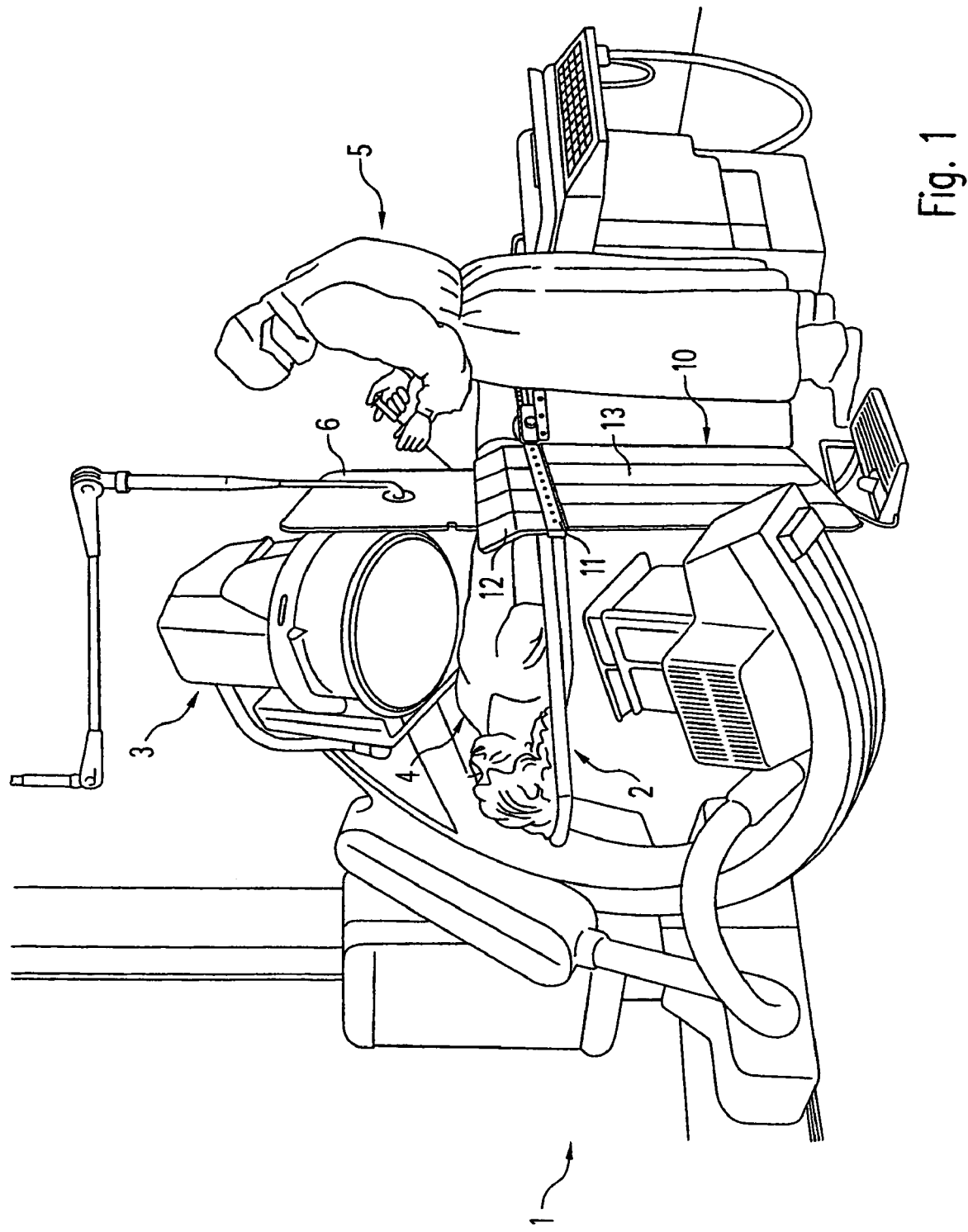
FIG. 1 shows an angiographic workstation at which the use of radiation protection arrangements according to the invention is provided.

FIG. 1 shows an angiographic workstation which is generally designated by the reference numeral 1 and whereof the essential components are a height-adjustable table 2 for the patient to lie on and an X-ray arrangement 3. The X-ray arrangement 3 is mounted to pivot in order to ensure as flexible as possible an alignment of the X-ray generator towards the patient 4. As a consequence of this, X-rays and the corresponding scattered radiation can be emitted in a wide variety of directions.

In order, therefore, to make it possible to protect a person 5 working at the workstation 1 from this radiation as comprehensively as possible, in addition to the clothing for protection against radiation worn by the person 5, additional measures to protect against radiation are provided. In the present case, these comprise a radiation protection panel 6 which is intended to enable the upper body and head of the doctor 5 carrying out treatment to be screened. Moreover, a lower body protection arrangement 10 is provided which is secured to the lateral region of the treatment table 2. This lower body protection arrangement 10 comprises an upper part 12, which is arranged on a carrier rail 11 secured to the table 2, and a plurality of slats 13 which are secured to the underside of the carrier rail 11 and are arranged to overlap laterally next to one another. The overlapping arrangement of the slats 13 results in a particularly high level of flexibility of the arrangement, which makes very effective radiation protection possible.

So that the radiation protection slats 13, which comprise lead sheets embedded in PVC, do not have to be cleaned or sterilized themselves, in accordance with the invention a cover is provided which can be pulled over the slats 13 to protect them. This will be explained below with reference to a first example embodiment in FIG. 2a.

Figure 2A:
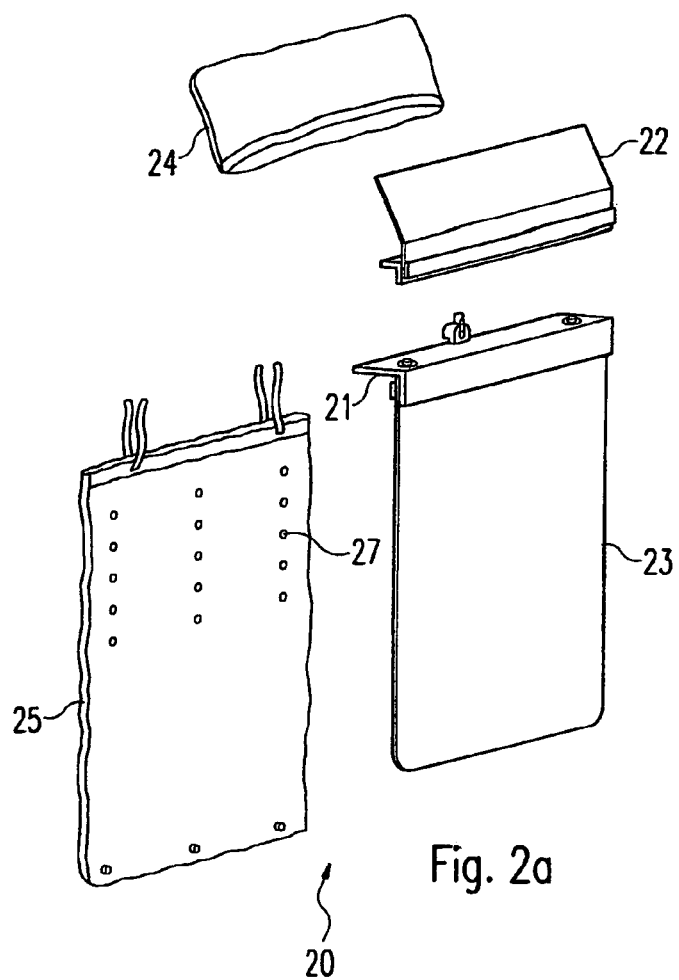
FIG. 2a shows the individual parts of a first example embodiment of a radiation protection arrangement according to the invention.

The lower body protection arrangement 20 illustrated in its individual parts in FIG. 2a comprises, first of all, the carrier rail 21 already mentioned above, to the upper side whereof an upper part 22 is to be secured. Towards the underside there extends a lead rubber blanket 23. The upper part 22 and the lead rubber blanker 23 have the lead sheets encased in PVC which have been mentioned above and each represent a screening element for screening the X-rays. The lead sheets themselves in this case have a lead equivalence value of at least 0.5 mm to make adequate screening possible.

The upper part 22 and the lead rubber blanket 23 should, as already mentioned, not or only infrequently be cleaned or sterilized, since this can only be carried out in a highly complex operation if the lead sheets are not to be damaged. For this reason, in each case covers 24 and 25 are provided which can be pulled onto the two screening elements 22 and 23 in a simple manner and which, for cleaning and sterilization, can be taken off again and taken away.

The cover 24 for the upper part 22 comprises a simple sheath which is pulled over the upper part 22. The cover 25 for the lower lead rubber blanket 23 also comprises a sheath which is approximately matched in its dimensions to the size of the lead rubber blanket 23 and is open to one side, and which is pulled onto the blanket 23 and secured to the carrier rail 21 by means of securing elements 26. In the example illustrated, the securing elements are formed by a plurality of cords 26, by means of which the cover 25 is bound firmly to the carrier rail 21. As an alternative to this, the cover 25 could, however, also be secured to the carrier rail 21 by means of a hook-and-burr closure or by press studs.

A particular feature of the cover 25 for the lower lead rubber blanket 23 consists in the provision of a plurality of rows of press studs 27. These can be used to turn up the cover 25 with the lead rubber blanket 23 received therein and to fix it in this turned-up position. The press studs 27 thus represent a fixing device which makes it possible to adjust the length of the radiation protection arrangement comprising the lead rubber blanket 23 and the cover 25. As a result, the overall length can be matched to the height of the treatment table, so that on the one hand radiation screening is achieved over the entire height, and on the other the possibility of the radiation protection arrangement lying on the floor and possibly being contaminated there by liquids is prevented. The important point is that the press studs 27 are arranged exclusively on the cover 25 and not on the lead rubber blanket 23 itself, since this—and in particular the lead sheet—would be damaged if buttons or similar elements were attached thereto.

FIG. 2a shows the radiation protection arrangement 20 in the assembled condition. As can be seen from the illustration, the screening elements 22 and 23 are completely surrounded by the covers 24 and 25, with the result that the screening elements 22 and 23 cannot themselves be soiled or contaminated. By contrast, the covers 24 and 25, which are preferably made from a material which is easy to clean and sterilize, for example the green cotton generally used in operating theaters, may be removed quickly and cleaned in a standard procedure. In this context, it is possible to change the covers 24 and 25 in the minimum of time, in particular even while treatment is still going on.

Figure 3:
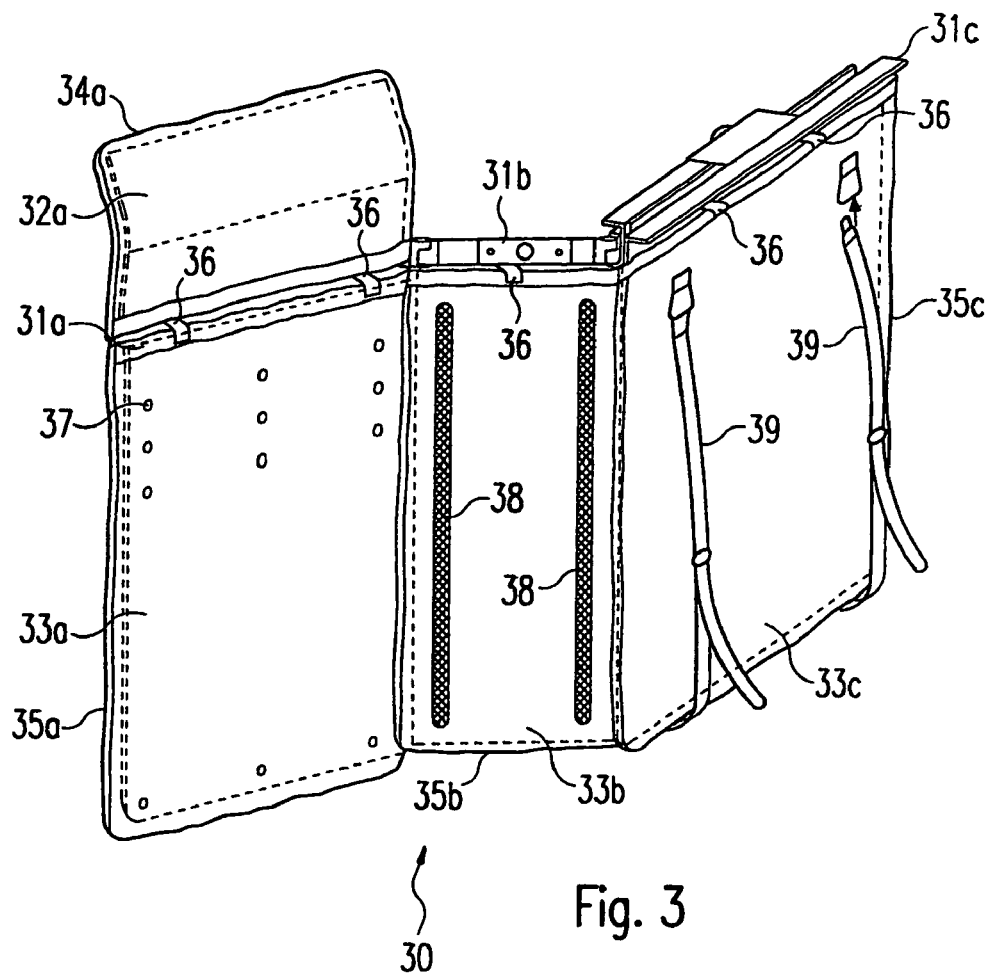
FIG. 3 shows a second example embodiment of a radiation protection arrangement according to the invention.

FIG. 3 shows a further example embodiment of a radiation protection arrangement 30 according to the invention. In the present case, this comprises three individual elements each having a carrier rail 31a to 31c, on the undersides whereof lead rubber blankets 33a to 33c are arranged. On the upper side of the first carrier rail 31a, a radiation protection upper part 32a having a corresponding cover 34a is furthermore provided. Here again, each individual lead rubber blanket 33a to 33c is provided with its own cover 35a to 35c which corresponds approximately to the size of the corresponding lead rubber blanket 33a to 33c in its width and length. Provided on the upper sides of the covers 35a to 35c are, once again, tapes 36 for securing them to the carrier rails 31a to 31c.

Figure 2B:
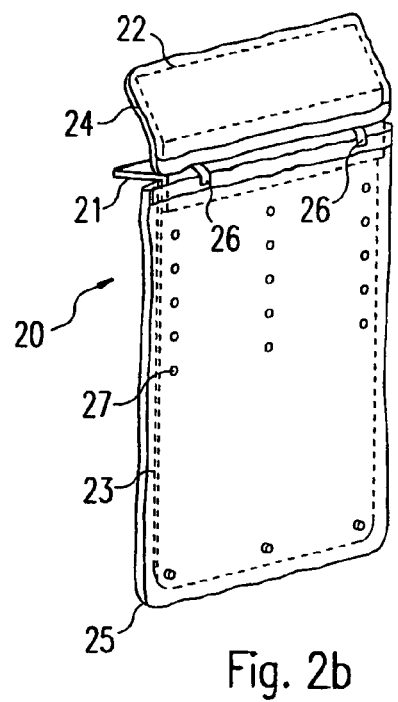
FIG. 2b shows the arrangement illustrated in FIG. 2a, in the assembled condition.

All three covers 35a to 35c have the fixing devices mentioned above, with the aid of which the length of the radiation protection arrangement can be varied. The first cover 35a has—like the cover illustrated earlier in FIGS. 2a and 2b—press studs 37. As an alternative to this, however, it is also possible to use a hook-and-burr closure, as illustrated in the middle arrangement. In this case, the cover 35b has two hook-type strips 38 which extend over the entire height so that when the lower end is flapped up the cover 35b can be fixed in the desired position, with the lead rubber blanket 33b, in a simple manner. A third possibility for adjusting the length consists in the use of ties 39, as provided in the case of the third cover 35c.

Figure 4:
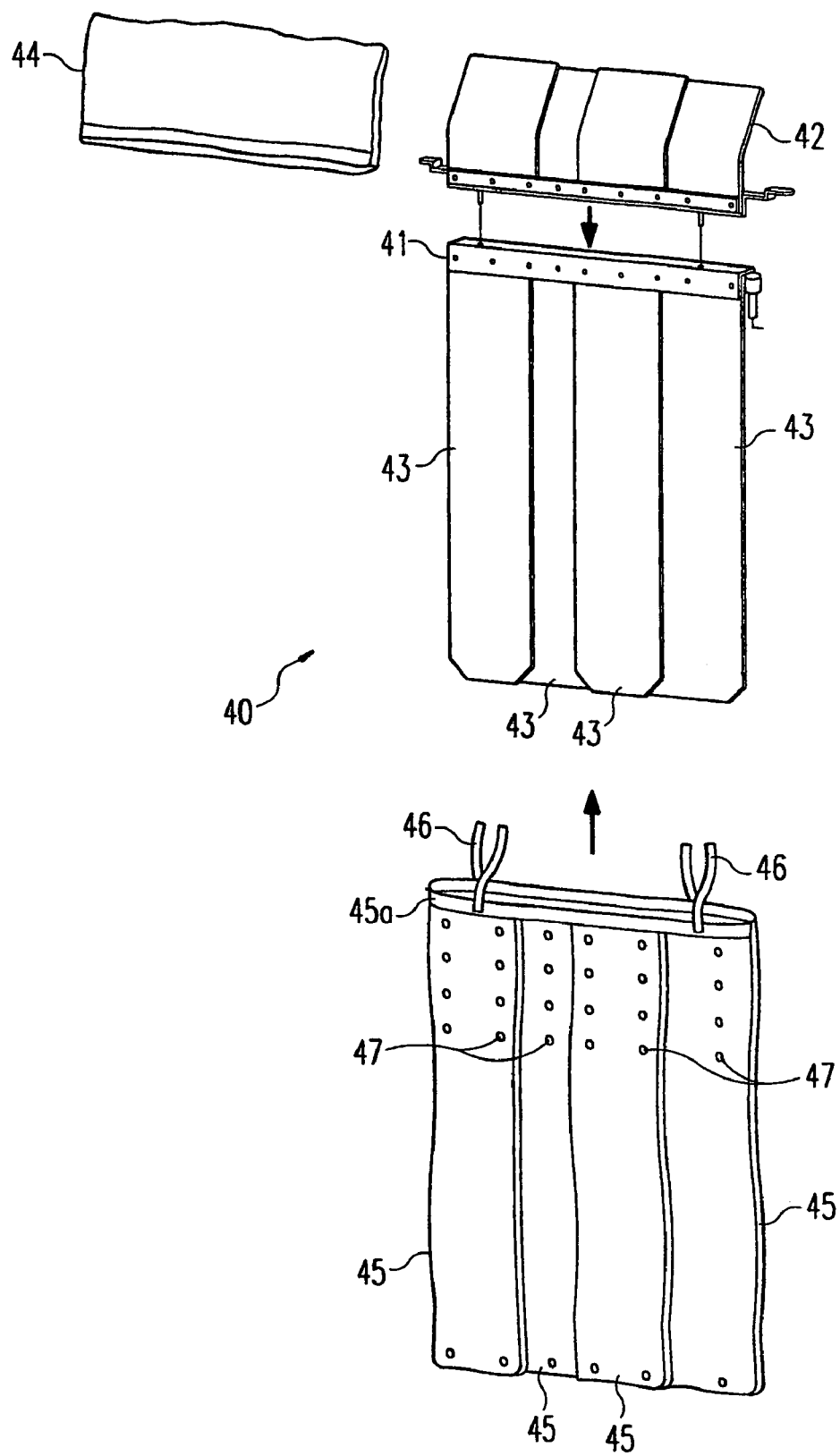
FIG. 4 shows a further example embodiment of a radiation protection arrangement which comprises a plurality of slats.

A particularly preferred example embodiment of a lower body protection arrangement is illustrated in FIG. 4. The radiation protection arrangement 40 illustrated here is characterized in that there are arranged on the underside of the carrier rail 41 not a single lead rubber blanket but, rather, a plurality of individual lead rubber slats 43 arranged laterally next to one another but overlapping. This overlapping arrangement of the slats 43 on the one hand makes effective protection from radiation possible, but on the other this arrangement is particularly flexible, with the result that optimum radiation protection is ensured even in the greatest variety of situations. Furthermore, an upper part 42 for radiation protection is once again provided, having a single cover 44.

In the present case, the cover for the individual slats 43 is formed by an arrangement which comprises a plurality of sheaths 45 arranged laterally next to one another and matched in their dimensions to the slats 43. The sheaths 45 are only connected to one another on their upper sides, by way of a common cuff 45a. Provided on this cuff 45a are, once again, the securing tapes 46 for securing the entire cover to the mounting strip 41.

In this preferred example embodiment too, the intention is to make it possible to adjust the height of the radiation protection arrangement, which is once again done by using press studs 47. Because each sheath 45 has its own press studs 47, the individual slats can even be adjusted in length individually. It goes without saying that hook-and-burr closures or ties could, however, also be used for height adjustability, as described above.

Figure 5:
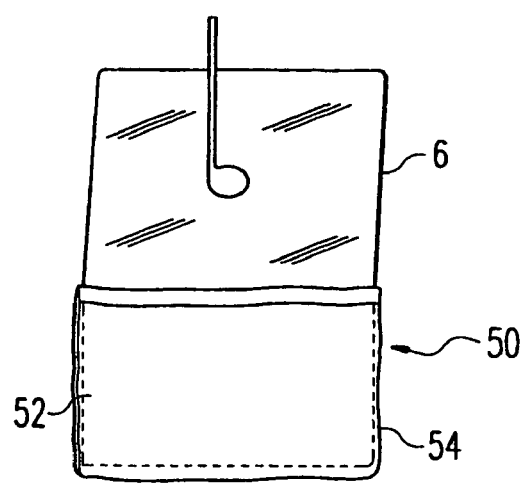
FIG. 5 shows a fourth example embodiment of a radiation protection arrangement for use on a radiation protection panel.

Finally, FIG. 5 is intended to illustrate a further example application of the radiation protection arrangement according to the invention. In this case, a screening element which is arranged on the underside of a radiation protection panel 6, as also illustrated in FIG. 1, is to be covered. The overall arrangement resulting from this is illustrated in FIG. 5.

Just as in the case of the lower body protection systems, a screening element 52 is secured to the lower edge of the radiation protection panel 6 and has the effect of an additional screening of the X-rays. This screening element once again comprises a PVC blanket including a lead sheet and enclosed within a cover 54. The cover 54 substantially corresponds in its construction to the covers provided for the lower body protection devices. One difference, however, consists in the fact that in this application there is no need for the radiation protection arrangement 50 to be height-adjustable, and accordingly fixing devices in the form of press studs, hook-and-burr closures or ties are not required. In this case too, however, there is the advantage that the cover 54 can be cleaned and sterilized in a simple manner without putting any stress on the sensitive screening element 52. It should furthermore be noted that, on the underside of the radiation protection panel 6, a radiation protection arrangement in accordance with the example embodiment of FIG. 4, that is to say with a plurality of overlapping slats, could also be provided, which is particularly advantageous if the lower edge of the panel 6 is not a straight line but is, for example, curved.

As a result of the present invention, it thus becomes possible to keep radiation protection arrangements clean and sterile in a simple manner. In particular in the case of lower body protection devices, it moreover opens up the possibility of making them adjustable in length and hence of adapting them to different situations.

The invention claimed is:

1. A radiation protection arrangement for screening radiation emitted by a radiation source, in particular an X-ray source, having
    a screening element which comprises or includes a radiation protection material, and
    a cover which is matched in shape to the screening element and completely surrounds the latter, it being possible to pull the cover over the screening element and completely separate it therefrom, and wherein, for the purpose of altering the length, there is provided a fixing device such that the cover, with the screening element arranged therein, is turnable up in at least one direction and fixed in the turned-up arrangement.

2. A radiation protection arrangement according to claim 1, wherein
    the cover comprises a material which can be sterilized using a suitable device or a suitable process.

3. A radiation protection arrangement according to claim 1, wherein
    the fixing device is formed by press studs.

4. A radiation protection arrangement according to claim 1, wherein
    the fixing device is formed by a hook-and-burr closure.

5. A radiation protection arrangement according to claim 1, wherein
    the fixing device is formed by a tie closure.

6. A radiation protection arrangement according to claim 1, wherein
    the cover has means for securing it to a carrier element which holds the screening element.

7. A radiation protection arrangement according to claim 6 wherein
    the means for securing are tapes.

8. A radiation protection arrangement according to claim 6, wherein
    the means for securing are press studs.

9. A radiation protection arrangement according to claim 6, wherein
    the means for securing are hook-and-burr closures.

10. A radiation protection arrangement according to claim 1, wherein
    the screening element is formed by a single blanket which includes an X-ray screening material, and the cover is formed by a sheath which is matched in its dimensions to the blanket and is open to one side.

11. A radiation protection arrangement according to claim 1, wherein
    the screening element comprises a plurality of slats arranged next to one another and including an X-ray screening material and are secured at one end to a common carrier element, the cover having a plurality of elongate sheaths for receiving a respective slat and connected to one another at one end by way of a common cuff.

12. A radiation protection arrangement according to claim 11, wherein
the slats are arranged such that they overlap.

13. A radiation protection arrangement according to claim 11, wherein
each sheath has its own fixing device for the purpose of altering the length.

14. A radiation protection arrangement according to claim 1, wherein
the screening element includes a lead sheet or lead rubber blanket surrounded by a PVC cover.

15. A radiation protection arrangement according to claim 14, wherein
the screening element has a lead equivalence value of approximately 0.5 mm.

16. A radiation protection arrangement according to claim 1, wherein
it is arranged on the underside of a radiation protection panel.

17. A radiation protection arrangement according to claim 1, wherein
it forms a lower body protection arranged to the side of a medical operating or treatment table.

18. A cover for a screening element which comprises or includes a radiation protection material and is provided for use in a radiation protection arrangement for screening radiation emitted by a radiation source, in particular an X-ray source, the cover being constructed such that it can be pulled over the screening element and completely separated therefrom again.

19. A cover according to claim 18, wherein
the cover comprises a material which can be sterilized using a suitable device or a suitable process.

20. A cover according to claim 18, wherein
for the purpose of altering the length, the cover can be turned up in at least one direction and fixed in the turned-up arrangement using a fixing device.

21. A cover according to claim 18, wherein
the cover is a sheath which is matched in its dimensions to the screening element and is open to one side.

22. A cover according to, claim 18, wherein
the cover has a plurality of elongate sheaths which are connected to one another at one end by way of a common cuff.

23. A cover according to, claim 22, wherein
each sheath has its own fixing device for the purpose of altering the length.

* * * * *